United States Patent
Xu et al.

(10) Patent No.: US 7,009,055 B2
(45) Date of Patent: Mar. 7, 2006

(54) PREPARATION OF SULFONYL QUINOLINE

(75) Inventors: Feng Xu, Staten Island, NY (US); Kimberly A. Savary, Rahway, NJ (US); John M. Williams, Hillsborough, NJ (US)

(73) Assignee: Merck & Co., Inc., Rahway, NJ (US)

( * ) Notice: Subject to any disclaimer, the term of this patent is extended or adjusted under 35 U.S.C. 154(b) by 94 days.

(21) Appl. No.: 10/484,610

(22) PCT Filed: Jul. 19, 2002

(86) PCT No.: PCT/US02/23308

§ 371 (c)(1),
(2), (4) Date: Jan. 20, 2004

(87) PCT Pub. No.: WO03/010137

PCT Pub. Date: Feb. 6, 2003

(65) Prior Publication Data

US 2004/0176604 A1    Sep. 9, 2004

Related U.S. Application Data

(60) Provisional application No. 60/307,440, filed on Jul. 24, 2001.

(51) Int. Cl.
*C07D 215/16*    (2006.01)

(52) U.S. Cl. .................. 546/177; 546/180; 568/34; 568/28

(58) Field of Classification Search ................ 546/177, 546/180; 568/34, 28
See application file for complete search history.

(56) References Cited

U.S. PATENT DOCUMENTS

| | | | | |
|---|---|---|---|---|
| 3,471,570 A | * | 10/1969 | Boesch et al. | 568/35 |
| 3,637,803 A | * | 1/1972 | Shen et al. | 560/11 |
| 3,689,567 A | * | 9/1972 | Shen et al. | 568/35 |
| 6,410,563 B1 | * | 6/2002 | Deschenes et al. | 514/314 |

OTHER PUBLICATIONS

Database Stn, Chem. Abst. Ca:135:76803, Deschenes, et al, 2001.

* cited by examiner

*Primary Examiner*—Johanna Richter
*Assistant Examiner*—Chukwuma Nwaonicha
(74) *Attorney, Agent, or Firm*—Curtis C. Panzer; David L. Rose

(57) ABSTRACT

A dibromomethyl moiety is converted to a sulfonylmethyl moiety by treatment with a sulfinic acid salt. For example, (methyl-sulfonyl)methyl bromo-quinoline is prepared by the treatment of dibromomethyl bromo-quinoline with a sulfinic acid salt.

5 Claims, No Drawings

PREPARATION OF SULFONYL QUINOLINE

CROSS REFERENCE TO RELATED APPLICATIONS

This application is the National Stage of International Application No. PCT/US02/23308, filed 19 Jul. 2002, which claims the benefit under 35 U.S.C. 119(3) of U.S. Provisional Application No. 60/307,440, filed 24 Jul. 2001.

BACKGROUND OF THE INVENTION

1. Field of the Invention

The present invention is directed to a method to prepare sulfonyl quinolines. In particular, this invention is directed to the preparation of sulfonyl quinolines by the treatment of dibromomethyl quinoline with a sulfinic acid salt.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3',5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3',5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

A major concern with the use of PDE4 inhibitors is the side effect of emisis which has been observed for several candidate compounds as described in C. Burnouf et al., ("Burnouf"), *Ann. Rep. In Med. Chem.*, 33:91–109(1998). B. Hughes et al., *Br. J. Pharmacol.*, 118:1183–1191(1996); M. J. Perry et al., *Cell Biochem. Biophys.*, 29:113–132(1998); S. B. Christensen et al., *J. Med. Chem.*, 41:821–835(1998); and Burnouf describe the wide variation of the severity of the undesirable side effects exhibited by various compounds. As described in M. D. Houslay et al., *Adv. In Pharmacol.*, 44:225–342(1998) and D. Spina et al., *Adv. In Pharmacol.*, 44:33–89(1998), there is great interest and research of therapeutic PDE4 inhibitors.

International Patent Publication WO9422852 describes quinolines as PDE4 inhibitors.

A. H. Cook, et al., *J. Chem. Soc.*, 413–417(1943) describes gamma-pyridylquinolines. Other quinoline compounds are described in Kei Manabe et al., *J. Org. Chem.*, 58(24):6692–6700(1993); Kei Manabe et al., *J. Am. Chem. Soc.*, 115(12):5324–5325(1993); and Kei Manabe et al., *J. Am. Chem. Soc.*, 114(17):6940–6941(1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

Methylsulfonyl quinolines, such as 6-(methylsulfonyl)methyl 8-bromo-quinoline, are important intermediates in the preparation of further substituted quinoline compounds such as 6-(methylsulfonyl)propyl 8-arylquinolines that are PDE4 inhibitors. There remains a need for such novel compounds and compositions that therapeutically inhibit PDE4 with minimal side effects. Accordingly, there is a need for improved methods of preparation of methylsulfonyl quinolines to lower the cost to make such PDE4 inhibitors.

SUMMARY OF THE INVENTION

The present invention is directed to the preparation of a sulfonylmethyl moiety by treating a dibromomethyl moiety with a sulfinic acid salt. For example, (Methyl-sulfonyl)methyl bromo-quinoline is prepared by the treatment of dibromomethyl bromo-quinoline with a sulfinic acid salt.

DETAILED DESCRIPTION OF THE INVENTION

The present invention forms a reaction product mixture substantially containing

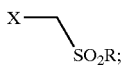

wherein X is an aryl or hetaryl, and R is a $C_{1-6}$alkyl or an aryl, by reacting

in an effective amount of a sulfinic acid salt ($RSO_2$ salt) in an effective amount of solvent.

An important intermediate in the preparation of 8-arylquinoline compounds is the formation of 8-bromoquinoline compounds so that the 8-bromo can be converted to the 8-aryl. Referring to the reaction schematic below, if the sulfonyl moiety is desired on the quinoline at the 6-position, the 6-methyl 8-bromoquinoline (1) is brominated—with a bromination reagent such as, for example, 1,3-dibromo-5,5-dimethylhydantoin, or N-bromosuccinimide ("NBS"), and a radical initiator—to the 6-bromomethyl 8-bromoquinoline (2) which can then be converted to 6-(methylsulfonyl)methyl 8-bromoquinoline (3) by treatment with a sulfinic acid salt such as sodium methanesulfinate. However, the bromination step (1) to (2) often forms unwanted products such as the 6-dibromomethyl 8-bromoquinoline (4) which usually is isolated and discarded before the sulfonation of 6-bromomethyl 8-bromoquinoline (2).

EXAMPLE 1

Preparation of 8-bromo-6-(methylsulfonyl)quinoline

A mixture of 6-bromomethyl 8-bromoquinoline (2) and 6-dibromomethyl 8-bromoquinoline (4) (2:4=3:1 mole ratio, with about 30 wt % succinimide) was obtained by bromination of the compound 1 in the presence of NBS and was carried through the sulfonation reaction. The presence of succinimide did not affect the sulfone formation and did simplify the isolation of the bromination product. To a slurry of the above mixture (15.0 g) in 48 mL of 20% water-DMAC was added sodium methane sulfinate (6.6 g, 64.8 mmol) in one portion at room temperature. The resulting solution was aged at room temperature until 2 was consumed (about 2h, by HPLC). Then, the reaction solution was allowed to warm up to 90° C. After 4h aging, the 6-dibromomethyl 8-bromoquinoline (4) was completely converted to product 3 (by HPLC). Then, the reaction solution was allowed to cool to room temperature and ½ saturated $NaHCO_3/H_2O$ solution (160 mL) was added over 1 h. The slurry was cooled to 0° C. and aged for 1 h before filtration. The wet cake was washed with a solution of 5:1 $DMAC:H_2O$ (2×20 mL) and then $H_2O$ (2×20 mL). After drying, 3 was obtained.

$^1$H NMR ($CDCl_3$, 400 MHz) δ 9.10 (dd, 1H, J=1.6 Hz, 4.2 Hz), 8.21 (dd, 1H, J=1.6 Hz, 8.3 Hz), 8.11 (d, 1H, J=1.9 Hz), 7.91 (d, 1H, J=1.9 Hz), 7.54 (dd, 1H, J=4.2 Hz, 8.3 Hz), 4.41 (s, 2H), 2.87 (s, 3H)ppm.

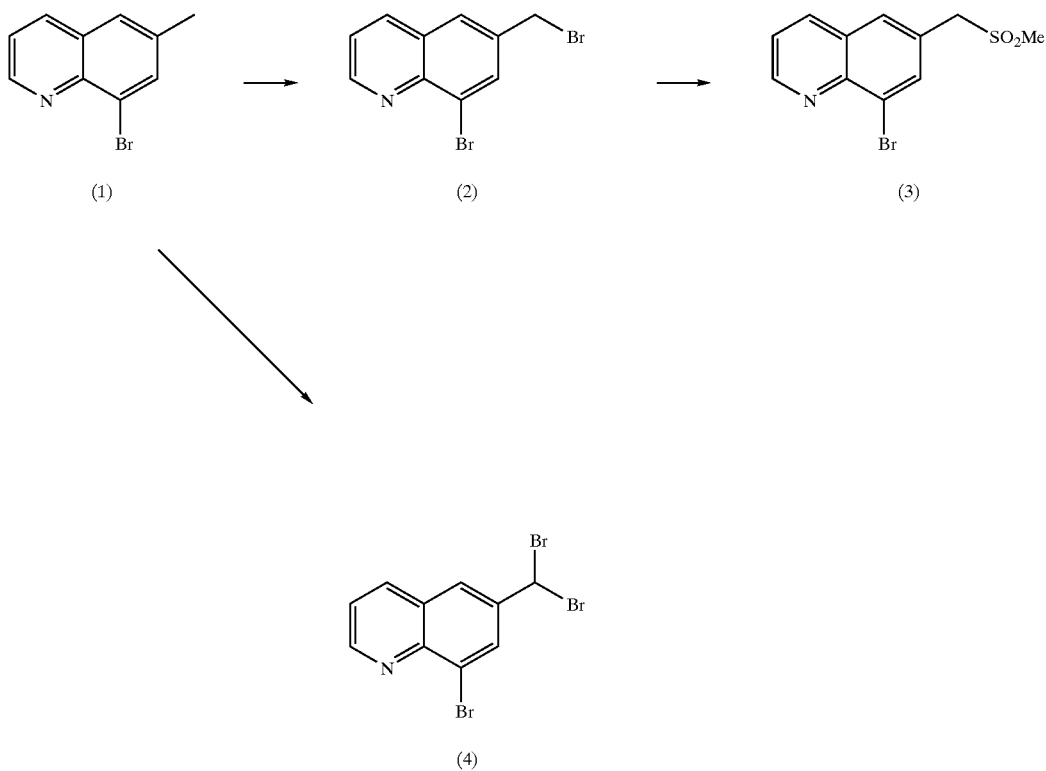

The present invention treats the tribromoquinoline (4) with a sulfinic acid salt such as sodium methanesulfinate to form the desired sulfone (3).

EXAMPLE 2

Preparation of (methylsulfonyl)(4-nitrophenyl)methane

A solution of 4-(dibromomethyl)-nitrobenzene (0.94 g, 3.2 mmol) and sodium methane sulfinate (1.63 g, 16.0 mmol) in 1.2 mL of water and 6 mL of N,N-dimethylacetamide was heated at 85° C. for 10 h. The reaction solution was allowed to cool to room temperature. Water (16 mL) was added dropwise over 1 h. The precipitated white solid was collected by filtration and washed with 4:1 $H_2O$: N,N-dimethylacetamide (5 mL) and water (5 mL). Suction drying provided EXAMPLE 2 as a white solid.

$^1$H NMR ($CDCl_3$, 400 MHz) δ 8.30 (d, 2 H, J=8.8 Hz), 7.64 (d, 2 H, J=8.8 Hz), 4.32 (s, 2H), 2.87 (s, 3H) ppm.

EXAMPLE 3

Preparation of 1-(((3-fluorophenyl)methyl)sulfonyl)4-methylbenzene

A solution of 3-fluorobenzal bromide (1.10 g, 4.1 mmol) and sodium p-toluenesulfinate (2.66 g, 14.93 mmol) in 1.8 mL of water and 6 mL of N,N-dimethylacetamide was heated at 110° C. for 10 h. The reaction solution was allowed to cool to room temperature. Water (20 mL) was added dropwise over 30 min. The precipitated white solid was collected by filtration and washed with water (5 mL). Suction drying provided EXAMPLE 3 as a white solid.

$^1$H NMR ($CDCl_3$, 400 MHz) δ 7.54 (m, 2 H), 7.27 (m, 2 H), 7.23 (m, 1H), 7.03 (m, 1 H), 6.90 (d, 1 H, J=7.63 Hz), 6.84 (m, 1 H), 4.28 (s, 2 H), 2.44 (s, 3 H) ppm.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected by a short $C_1$–$C_2$alkyl length to the oxy connecting atom.

The term "$C_0$–$C_6$alkyl" includes alkyls containing 6, 5, 4, 3, 2, 1, or no carbon atoms. An alkyl with no carbon atoms is a hydrogen atom substituent.

The term "aryl" means an aromatic substituent which is a single ring or multiple rings fused together. When formed of multiple rings, at least one of the constituent rings is aromatic. The preferred aryl substituents are phenyl and naphthyl groups.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five member ring containing from 5 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "amine" unless specifically stated otherwise includes primary, secondary and tertiary amines.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring.

Other variations or modifications, which will be obvious to those skilled in the art, are within the scope and teachings of this invention. This invention is not to be limited except as set forth in the following claims.

What is claimed is:

1. A method of forming a reaction product mixture substantially containing

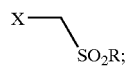

wherein X is an aryl or heteroaryl, and R is a $C_{1-6}$ alkyl or aryl, said method comprising:
reacting

in an effective amount of a sulfinic acid salt ($RSO_2$ salt) in an effective amount of solvent.

2. The method according to claim 1, wherein X is a quinoline optionally substituted with halogen, —$C_1$–$C_6$alkyl, —$NO_2$, —CN, or —$C_1$–$C_6$alkoxy.

3. The method according to claim 1, wherein the sulfinic acid salt is sodium methanesulfinate.

4. A method of forming a reaction product mixture substantially containing:
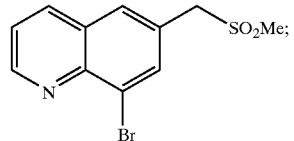
said method comprising:
reacting
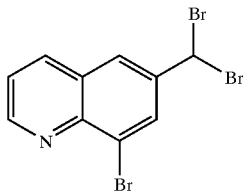
in an effective amount of a sulfinic acid salt in an effective amount of solvent at an effective temperature.
5. The method according to claim 4, wherein the sulfinic acid salt is sodium methanesulfinate.
* * * * *